(12) United States Patent
Boffelli et al.

(10) Patent No.: US 7,148,322 B2
(45) Date of Patent: Dec. 12, 2006

(54) PROCESS FOR THE PREPARATION OF ECHINOCANDIN DERIVATIVES

(76) Inventors: Philippe Boffelli, 21 rue des Polyanthas, 93110 Rosny Sous Bois (FR); Agnes Brouillard, 45, Allee du Jardin Anglais, F-93340 Le Rainey (FR); Colette Colladant, 26, Rue Richard Gardebled, F-93110 Rosny Sous Bois (FR); Serge Droux, 43, Rue des Sablons, 77230 Dammartin En Goele (FR); Michel Elter, 23 Chemin de la Carrière, 95410 Groslay (FR); Didier Ferroud, 26 rue des Feux Frères, 93700 Drancy (FR); Guy Lemaitre, 62 Avenue des Chataigniers, 77280 Othis (FR); Joseph Paladino, 604 Grande Rue, 01600 Reyrieux (FR)

( * ) Notice: Subject to any disclaimer, the term of this patent is extended or adjusted under 35 U.S.C. 154(b) by 0 days.

(21) Appl. No.: 10/867,070

(22) Filed: Jun. 14, 2004

(65) Prior Publication Data

US 2005/0032679 A1    Feb. 10, 2005

Related U.S. Application Data

(63) Continuation of application No. PCT/FR02/04308, filed on Dec. 12, 2002.

(30) Foreign Application Priority Data

Dec. 14, 2001  (FR)  .................................. 01 16230

(51) Int. Cl.
*C07K 1/00*    (2006.01)
*C07K 2/00*    (2006.01)
*C07K 7/64*    (2006.01)
*A61K 38/00*   (2006.01)
*A61K 38/02*   (2006.01)
*A61K 38/12*   (2006.01)

(52) U.S. Cl. .............................. 530/333; 514/2; 514/9; 514/11; 530/300; 530/317

(58) Field of Classification Search ................ 530/333; 514/2, 11
See application file for complete search history.

(56) References Cited

U.S. PATENT DOCUMENTS

| | | | | |
|---|---|---|---|---|
| 5,539,122 A | * | 7/1996 | Kempf et al. ................ | 548/204 |
| 5,552,520 A | * | 9/1996 | Kim et al. ................... | 530/311 |
| 5,668,105 A | * | 9/1997 | Balkovec et al. ............. | 514/11 |
| 6,207,710 B1 | * | 3/2001 | Audia et al. ................. | 514/551 |
| 2004/0072737 A1 | * | 4/2004 | Courtin et al. ................ | 514/9 |

FOREIGN PATENT DOCUMENTS

AU          199915659 B2  *  12/1998
AU          199915659 B2  *  6/1999

OTHER PUBLICATIONS

Encyclopedia of Reagents for Organic Synthesis, 1995, John Wiley & Sons, vol. 4 (Dip-K), pp. 2694-2695.*
L.A. Carpino and A. El-Faham. J. Org. Chem. (1994) 59(4), pp. 695-698.*
R.J. Bastin. Org. Proc. Res. Dev. (2000) 4, 427-435.*
M. Forest and A. Fournier. Int. J. Peptide Protein Res. (1990) 35, pp. 89-94.*
J. Jezek and R.A. Houghten. Collect. Czech. Chem. Commun. (1994) 59, pp. 691-706.*
R. Traber, et al. Helvetica Chimica Acta (1979) 62(4) pp. 1252-1267.*
T. Brossette, et al. Tetrahedron (2001) 57, pp. 8129-8143.*

* cited by examiner

*Primary Examiner*—Cecilia J. Tsang
*Assistant Examiner*—Andrew D. Kosar
(74) *Attorney, Agent, or Firm*—Harness, Dickey & Pierce, P.L.C.

(57) ABSTRACT

A subject of the invention is a process for the preparation of the compounds of formula (I):

R being as defined in the description as well as their salts, the intermediates, the use of the dihydrochloride as a medicament and the pharmaceutical compositions containing them. The process for preparing formula (I) leads to greater than 50% yields of isomer A, and its intended use, e.g. as an antifungal medicament.

20 Claims, No Drawings

PROCESS FOR THE PREPARATION OF ECHINOCANDIN DERIVATIVES

RELATED APPLICATION DATA

This application is a continuation of International Application No. PCT/FR02/04308, filed Dec. 12, 2002; and also claims the benefit of priority from French Patent Application No. 0116230, filed Dec. 14, 2001; the disclosures of which are incorporated herein by reference.

BACKGROUND OF THE INVENTION

A subject of the present invention is a process for the preparation of echinocandin derivatives, the intermediates and the products obtained and their use as an antifungal medicament.

Numerous compounds having an antifungal activity are known in the prior art. In particular the echinocandin derivatives as defined in International Application WO99/29716 can be mentioned.

The objective of the present invention is to provide a new process for the preparation of echinocandin derivatives and to obtain new salts of the latter.

Echinocandin can be presented in the form of two epimers called isomer A and isomer B corresponding to the R and S configurations of the substituent in position 4. One of the subjects of the present invention is to obtain during the process, a majority of one of the two isomers, i.e. at least greater than 50% (isomer called form A, corresponding to the pharmacologically active compound of formula (I), which is not the case for the process according to WO99/29716 during which the active isomer A obtained during the process before purification on a chromatographic column is in the minority.

Moreover another objective of the present invention is to avoid purifications of the intermediate products by chromatography and to obtain crystallized products which allows a significant improvement in yields.

SUMMARY OF THE INVENTION

Therefore a subject of the invention is a process for the preparation of compounds of formula (I)

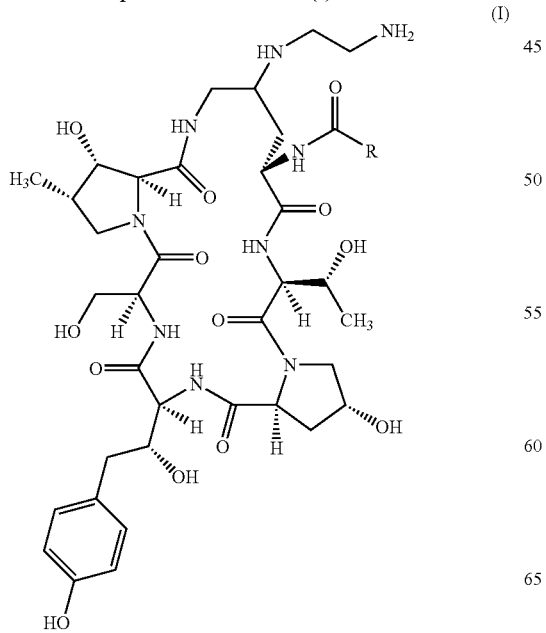

in which R represents a linear or branched or cyclic chain containing up to 30 carbon atoms, optionally containing one or more heteroatoms and one or more heterocycles comprising the following stages a) A compound of formula (II)

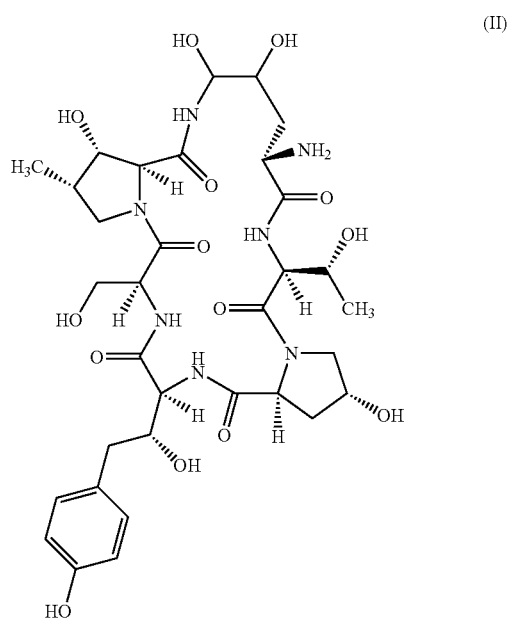

is subjected to the action of an acid of formula $R-CO_2H$, R being as defined above, said acid being, if appropriate, in an isolated or non isolated activated form, in order to obtain the compound of formula (III)

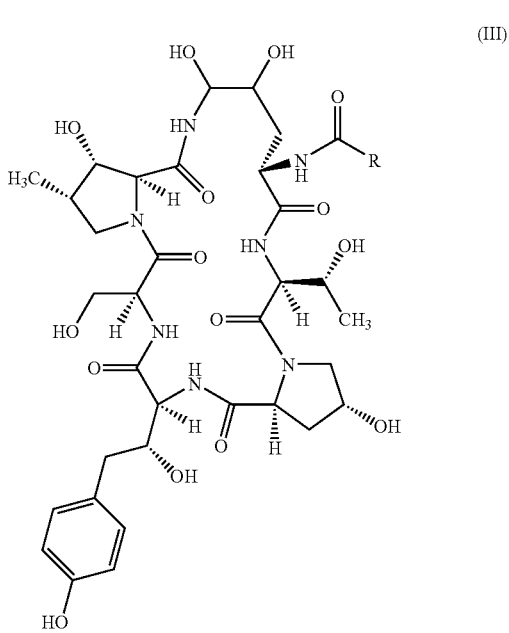

b) if appropriate, the compound of formula (III) is subjected to an alkylation reaction of the alcohol in position 5 by the action of an alcohol of formula Alk-OH in the presence of PPTS, Alk being an Alkyl radical containing 1 to 4 carbon atoms, in order to obtain the compound of formula (III')

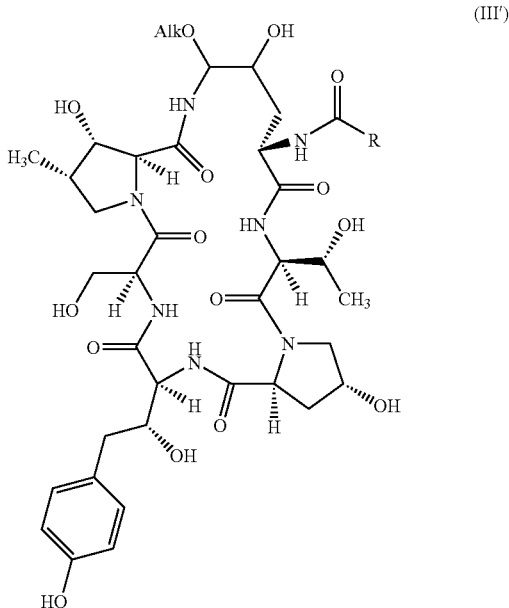

(III')

c) the compound of formula (III) or (III') is subjected to a dehydration reaction, in order to obtain a compound of formula (IV)

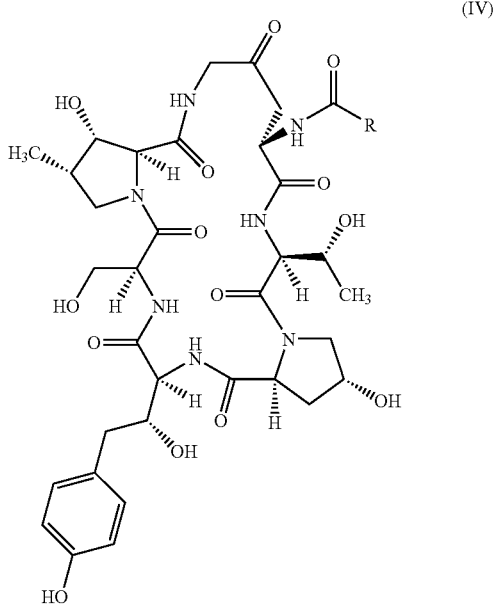

(IV)

d) the compound of formula (IV) is subjected to a reducing amination reaction by the action of ethylene diamine in the presence of a reducing agent such as $NaBH_3CN$ in the presence of a Lewis acid, or $NaBH(OCOR'_3)$, OCOR' representing Boc-L-Pro, Bzl-L-Pro or any other optically active amino acid as well as any other chiral or non chiral carboxylic acid, in order to obtain the compound of formula (I) as defined above, comprising a majority of one of the active isomers, said compound of formula (I) then being subjected, if appropriate, and in any appropriate order to the one or more of the following operations purification by chromatography
purification by crystallization
the action of a base
salification.

DETAILED DESCRIPTION

Preferably a subject of the invention is a process as defined previously in which the compounds of formulae (I), (III), (III') or (IV) contain an R radical representing the following groups:

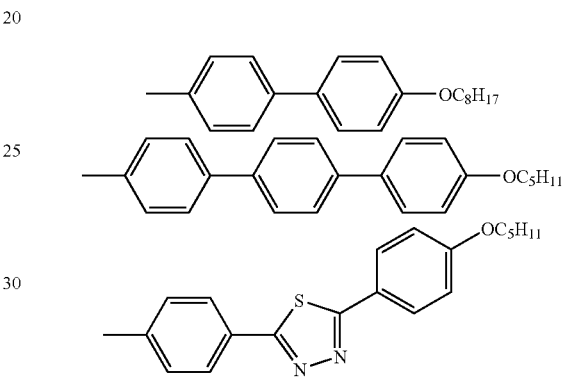

Preferably, a subject of the invention is a process as defined previously in which the compounds of formulae (I), (III), (III') or (IV) contain an R radical representing the following group:

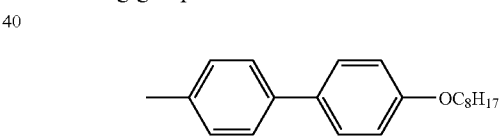

The compound of formula (II) is prepared according to the method described in the International Application WO99/29716 page 18 (Preparation 2, "nucleus of deoxymulundocandin").

Activation of the acid of formula $R-CO_2H$ is carried out according to standard methods known to a person skilled in the art (Journet M. et al, J. Org. Chem. (1999), 64, 2411–2417; Pöchlauer P. et al. Tetrahedron 54(1998) 3489–3494; Kunushima et al. Tetrahedron (1999) 55 13159–13170). In particular pentaflurophenol is used in order to obtain the activated ester of pentafluorophenol which is isolated before being used in the acylation reaction of the amine. Another method is the use of N-hydroxysuccinimide (optionally N-hydroxybenzotriazole) in order to obtain the activated ester of N-hydroxysuccinimide (optionally N-hydroxybenzotriazole) which is also isolated.

The acylation stage which follows in order to obtain a compound of formula (III) is carried out in the presence of a base according to methods known to a person skilled in the art and is illustrated in the examples described hereafter. It is also possible to carry out the acylation without isolating the active ester and without an added base by operating in the presence of 4-(4,6-dimethoxy-1,3,5-triazin-2-yl)-4-myl-morpholinium chloride (DMTMM). This last alternative has the advantage of suppressing an isolation stage and therefore of improving yields.

The dehydration stage of the compound of formula (III) in order to obtain a compound of formula (IV) can be carried out in the following way:

The dehydration stage is carried out in the presence of a hydrohalogenated acid such as HBr in the presence of $MgI_2$. In this case, it is not necessary to pass via the intermediate of formula (III').

By way of a variant, it can be desirable to alkylate the hydroxyl group in position 5 before proceeding to the dehydration stage. For example methylation can be carried out with methanol in the presence of PPTS (Pyridinium Paratoluene Sulphonate) in order to obtain a compound of formula (III') with Alk representing a methyl.

Finally, this dehydration reaction can also be carried out in the presence of alpha-acetoxy isobutyryl bromide (AIBB) in dioxane. In this latter case the operation can be carried out either on the compound of formula (III') or directly on the compound of formula (III) in the presence of $MgI_2$.

Preferably, the compound obtained after the dehydration reaction is then purified by crystallization from a mixture of DMF(dimethylformamide)/MeCN (acetonitrile). Mixtures of the following solvents: DMF/acetone and DMF/AcOEt (ethyl acetate) can also be used.

The reducing amination reaction of the compounds of formula (IV) in order to obtain the echinocandin of formula (I) is carried out according to the methods described in the literature and known to a person skilled in the art (Yamada K. et al. J. Chem. Soc. Perkin Trans I (1983) 265–270; Hutchins R. et al. Org. prep. Proc. Int. 11 (5) (1979) 201–246). In particular ethylenediamine is used in the presence of $NaBH_3CN$ by coupling with $TiCl_4$ or any other Lewis acid or in the presence of $NaBH(OCOR')_3$, OCOR' representing Boc-L-Pro, Pro, Bzl-L-Pro or any other optically active amino acid as well as any other chiral or non chiral carboxylic acid.

Coupling the reduction reagent $NaBH_3CN$ with a Lewis acid, in particular $TiCl_4$, is an essential element for selectivity and therefore in order to obtain a mixture of isomer A and isomer B in which the active isomer A is in the majority. In general a ratio of isomer A of greater than 70%, and in particular comprised between 80 and 85% is obtained. The situation is similar with the other reagents mentioned above.

In particular, for the compound of formula (Ia), in this stage an isomer A/isomer B ratio is obtained of 80–85%/20–15% respectively whereas the process as described in WO 97/29716 leads to a mixture in which isomer A is in the minority or equivalent (racemic A and B mixture).

During the reducing amination stage, a reaction intermediate before reduction can if appropriate, be isolated, and is therefore a subject of the present invention. It is an imidazolidine of formula (IV') or (IV'a) when R represents a -Ph-Ph-O—$C_8H_{17}$ group

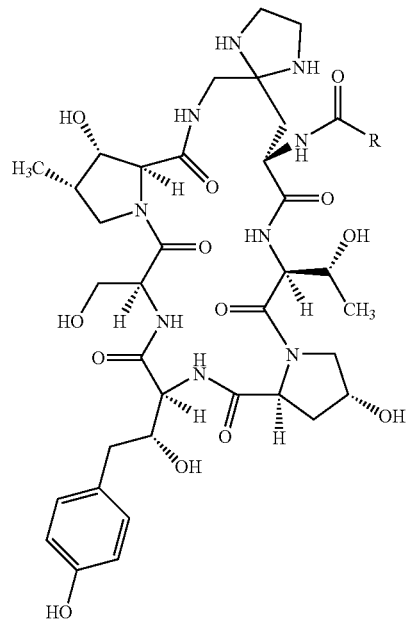

It can be desirable to purify the product or products obtained by chromatography or by recrystallization. This operation is carried out according to the usual methods known to a person skilled in the art. When the product obtained is in particular in the form of a trifluoroacetic acid salt following chromatography, it is desirable to eliminate this salt by the action of a base in order to obtain the compound of formula (I) in the form of a base.

The salification reaction is carried out according to the usual methods known to a person skilled in the art. Preparation of the hydrochloride or of the di-hydrochloride is carried out in the presence of hydrochloric acid in methanol.

Quite particularly, a subject of the present invention is a process for the preparation of the compounds of formula (Ia)

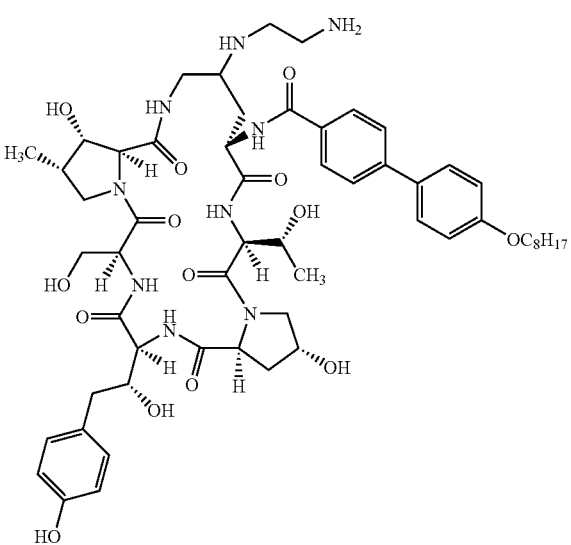

(Ia)

comprising the following stages a) A compound of formula (II)

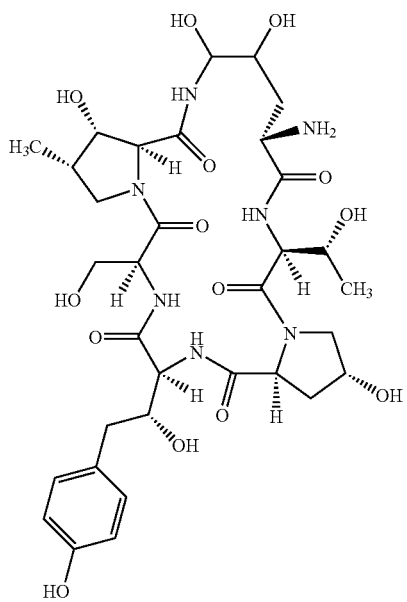

is subjected to the action of an acid of formula $C_8H_{17}$—O-Ph-Ph-$CO_2H$, said acid being, if appropriate, in an activated, isolated or non isolated form, in order to obtain the compound of formula (IIIa)

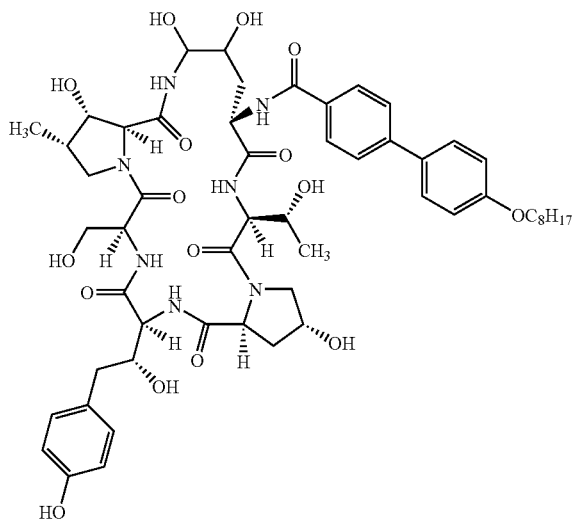

b) if appropriate the compound of formula (IIIa) is subjected to an alkylation reaction of the alcohol in position 5 by the action of methanol in the presence of PPTS in order to obtain the compound of formula (IIIa')

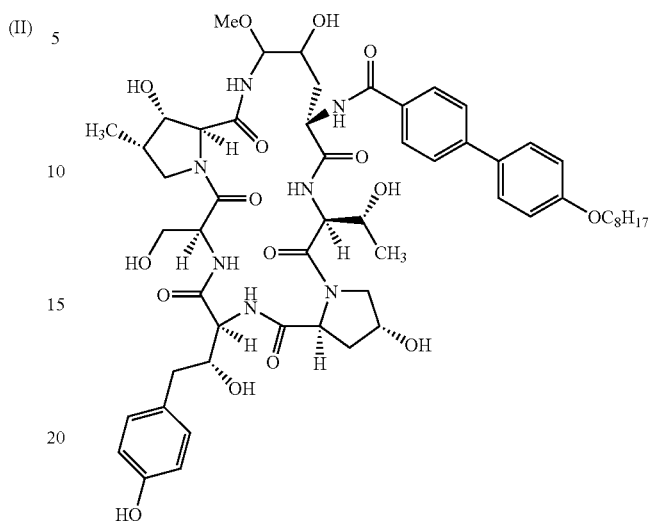

c) the compound of formula (IIIa) or (IIIa') is subjected to a dehydration reaction, in order to obtain a compound of formula (IVa),

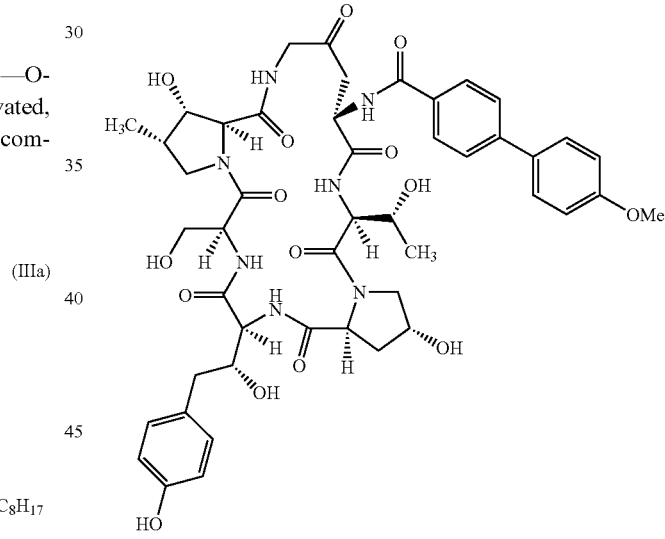

d) the compound of formula (IVa) is subjected to a reducing amination reaction by the action of ethylene diamine in the presence of a reducing agent such as $NaBH_3CN$ coupled with $TiCl_4$, NaBH(Boc-L-pro)$_3$ or NaBH(Bzl-L-Pro)$_3$ in order to obtain the compound of formula (Ia) as defined above, comprising a majority of one of the active isomers, said compound of formula (Ia) being subjected to one or more of the following operations in an appropriate order chromatography
crystallization
the action of a base
salification by the action of hydrochloric acid.

The compound of formula (Ia) can be found in the form of a mixture of two epimers (asymmetrical carbon in position 4) which are called isomer A or isomer B. The compound of formula (I) obtained according to the process as defined above allows a mixture of isomer A/isomer B of approximately 70–85%/30–15% to be obtained.

The purification/crystallization and salification stages which are carried out after the reducing amination reaction allows the active epimer A of the compound of formula (Ia) to be obtained selectively.

Preferably, the compound of formula (Ia) is purified by chromatography on silica then by reversed-phase chromatography using a mixture of organic solvents, water and trifluoroacetic acid in order to obtain the trifluoroacetic acid salt of the compound of formula (Ia). This salt is then subjected to the action of a base, for example by the action of an aqueous solution of sodium bicarbonate, in order to obtain the compound of formula (Ia) in the form of a base. Then, the base obtained is salified by the action of hydrochloric acid in order to obtain the corresponding salt namely the dihydrochloride of the compound of formula (Ia).

Therefore a quite particular subject of the invention is a process as defined previously characterized in that the compound of formula (Ia) is subjected successively to the following operations:
a) purification by chromatography on silica then by reversed-phase chromatography using a mixture of organic solvents, water and trifluoroacetic acid in order to obtain the trifluoroacetic acid salt of the compound of formula (Ia)
b) the action of a base, for example, by the action of an aqueous solution of sodium bicarbonate, in order to obtain the compound of formula (Ia) in the form of a base
c) salification by the action of hydrochloric acid in order to obtain the corresponding salt namely the dihydrochloride of the compound of formula (Ia).

Therefore a quite particular subject of the invention is a process as defined previously characterized in that the activation reaction of the acid is carried out in the presence of pentafluorophenol, N-hydroxysuccinimide or optionally N-hydroxybenzotriazole.

Therefore a quite particular subject of the invention is a process as defined previously characterized in that the acylation reaction in the presence of an isolated activated acid, is carried out in the presence of diisopropylethylamine.

Therefore a quite particular subject of the invention is a process as defined previously characterized in that the activation reaction then the acylation reaction in the presence of an isolated activated acid, is carried out in the presence of N-methylpyrrolidone and DMTMM.

Therefore a quite particular subject of the invention is a process as defined previously characterized in that the dehydration reaction is carried out in the presence of AIBB and if appropriate $MgI_2$.

Therefore a quite particular subject of the invention is a process as defined previously characterized in that the dehydration reaction is carried out in the presence of HBr—AcOH and $MgI_2$.

Therefore a quite particular subject of the invention is a process as defined previously characterized in that the product originating from the dehydration is purified by crystallization from a dimethylformamide (DMF)/acetonitrile, DMF/acetone or DMF/AcOEt mixture.

Therefore a quite particular subject of the invention is a process as defined previously characterized in that the reducing amination reaction is carried out in the presence of a reducing agent chosen from $NaBH_3CN$ coupled with $TiCl_4$, NaBH (Boc-L-Pro)$_3$ or NaBH (Bzl-L-Pro)$_3$.

Therefore a subject of the invention is also the dihydrochloride of 1-[4-[(2-aminoethyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B in 4S or 4R form or in the form of a mixture of the two stereoisomers.

The process as described previously allows isomer A of the compound of formula (I) or (Ia) to be obtained in the majority before separation of the isomers by chromatography.

Therefore a subject of the invention is also the dihydrochloride of 1-[4-[(2-aminoethyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B in the form of the active isomer A obtained by the process as described previously.

A subject of the invention is also the dihydrochloride of 1-[4-[(2-aminoethyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B in 4S or 4R form or in the form of a mixture of the two stereoisomers, as a medicament and in particular as and antifungal medicament.

Finally, a subject of the invention is the pharmaceutical compositions containing the dihydrochloride of 1-[4-[(2-aminoethyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B in 4S or 4R form or in the form of a mixture of the two stereoisomers and a pharmaceutically acceptable vehicle.

1-[4-[(2-aminoethyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B is prepared in WO 99/29716 in the form of a base or the trifluoroacetic acid salt (Example 14). The dihydrochloride has the advantage of having a better stability and solubility in water. Moreover, the dihydrochloride is the preferred pharmaceutically acceptable salt which is a subject of the present invention.

EXAMPLE 1

Dihydrochloride of 1-[4-[(2-aminoyl)amino]-N-2-[[4'-(octyloxy)[1,1'-biphenyl]-4-yl]carbonyl]-L-ornithine]-4-[4-(4-hydroxyphenyl)-L-threonine]-5-L-serine echinocandin B I): First Stage: Acylation of the Compound of Formula (II) and Obtaining a Compound of Formula (IIIa)

1-[(4R, 5R)-4,5-dihidroxy-N2-[[4'-(octyloxy)[1,1'-biphenyl]-4-yl]carbonyl]-L-ornithine]-4-[4-(4-hydroxyphenyl)-L-threonine]-5-L-serine echinocandin B Route 1: by the Activated Ester of Isolated Pentaflurophenol Stage 1: Preparation of the Activated Ester Pentafluorophenyl 4'-Octyloxy-biphenyl-4-carboxylate 100 g of 4-octyloxybiphenyl-4'carboxylic acid and 62 g of pentafluorophenol are introduced into 1 liter of dichloromethane. Agitation is carried out for 15 minutes and 69.6 g of N,N'-dicyclohexylcarbodiimide in solution in 500 ml of dichloromethane is added over 15 minutes. The dark beige suspension is agitated for 20 hours at ambient temperature. The dicyclohexylurea is filtered and the filtrate is concentrated. Distillation to constant volume is carried out by the regular addition of ethanol up to the vapour temperature of 74° C. The reaction medium is cooled down to ambient temperature, followed by agitating for one hour, filtering then washing with ethanol. After drying, 145.7 g of sought product is obtained in the form of crystals.

Yield 96.5% NMR (CDCl$_3$): 8.23–7.72 (AA'BB') 4H; 7.01–7.60 (AA'BB') 4H; 4.02 (t) 2H; 1.82 (quint) 2H; 1.48 (quint) 2H; 1.32 (m) 8H; 0.89 (t) 3H.

Stage 2: Acylation 23.2 g of the compound of formula (II) ("nucleus of deoxymuluncandin" prepared according to Preparation 2 of WO 99/29716) and 14.1 g of the ester obtained above in 60 ml of DMF are introduced. 6.7 ml of diisopropylethylamine is introduced into the suspension and agitation is carried out for 24 hours under a nitrogen atmosphere at ambient temperature. The homogenous reaction medium is poured into one liter of water over 10 minutes whilst moderate agitation is carried out, the suspension is agitated for 2 hours, filtered and the solid washed with water. The solid is dried under vacuum at room temperature then taken to reflux in 100 ml of methylene chloride, under nitrogen whilst agitating for 2 hours (40° C.), followed by cooling down to ambient temperature over 1 hour, agitating for 1 hour, filtering the solid and rinsing it three times with methylene chloride and drying under vacuum at room temperature. 26.9 g of expected product is obtained in the form of a beige solid.

Yield 91.5% TLC: Rf :0.13 silica plate; development UV 254 nm; eluant: CH$_2$Cl$_2$-MeOH-water: 86-13-1 NMR: (DMSO) Threonine: 8.16 (1H), 4.85 (1H), 4.41 (1H), 1.13 (3H); γHydroxyproline: 4.42 (1H), 1.92–2.28 (2H), 4.44 (1H), 3.86–3.70 (2H); βHydroxy homo tyrosine 7.36 (1H), 4.23 (1H), 4.20 (1H), 2.53–2.46 (2H), 6.98 (2H), 6.68 (2H); Serine: 7.40 (1H), 4.86 (1H), 3.66–3.60 (2H), βHydroxy γmethyl proline: 4.27 (1H), 4.03 (1H), 2.38 (1H), 0.99 (3H), 3.25–3.93 (2H), <<ornithine >>: 7.98 (1H), 5.16 (1H), 3.96 (1H), 8.54 (1H), 4.44 (1H), 1.98 (2H); Aromatic and octyloxy chain: 7.98 (2H), 7.71 (2H), 7.68 (2H), 7.02 (2H), 4.00 (2H), 1.72 (2H), 1.41 (2H), 1.28 (2H), 1.25 (2H), 1.31 (2H), 1.27 (2H), 0.86 (3H).

Route 2: by the Activated Ester of Isolated HOSu

Stage 1: Synthesis of the Activated Ester 2,5-dioxo-pyrrolidine
4'-octyloxy-biphenyl-4-carboxylate 9.3 g of octyloxybiphenyl acid, 93 ml of dichloromethane, 3.8 g of N-hydroxysuccinimide, 6.3 g of EDC are introduced and agitation is carried out for 3 hours at ambient temperature. 6 ml of water is added, agitation is carried out for 10 minutes, followed by decanting and reextracting with 45 ml of dichloromethane. The organic phase is washed with water (3 times 45 ml) and dried over sodium sulphate. After bringing to dryness under vacuum, 12.05 g of expected product is obtained in the form of crystals.

Yield: 99.9% NMR: CDCl$_3$: 8.2–7.65 (AA'BB') 4H; 7.6–6.97 (AA'BB') 4H; 4.02 (t, 2H); 2.93 (broad) 4H; 1.83 (quint 2H); 1.45 (m) 2H; 1.3 (m) 8H; 0.9 (t) 3H.

Stage 2: Acylation 1.43 g of succinimidic ester as prepared above is dissolved in 6 ml of DMF. 2.42 g of "nucleus of deoxymuluncandin" (prepared according to Preparation 2 of WO 99/29716) and 0.66 ml of diisopropylethylamine are introduced. The solution is agitated for 18 hours at ambient temperature. 35 ml of water is introduced and agitated is carried out for 2 hours at ambient temperature. After filtering, the solid is taken up in 30 ml of water under agitation for 2 hours in a reaction vessel, followed by filtering and rinsing with water. The solid is dried under vacuum at ambient temperature and 2.75 g of expected product is obtained in the form of beige solid.

Yield 98.2%

Route 3: Synthesis by Direct Activation with DMTMM 2.8 g of deoxymuluncandin (prepared according to Preparation 2 of WO 99/29716) is dissolved in 8.3 ml of N-myl pyrolidone. 1.12 g of octyloxybiphenyl acid and 0.95 g of 4-(4,6-Dimoxy-1.3,5-triazin-2-yl)-4-myl-morpholinium chloride (DMTMM) is added. After agitation for 24 hours at ambient temperature, the reaction medium is poured into 133 ml of water under agitation. Agitated is carried out for 20 minutes, the solid is filtered and rinsed 3 times with water (3 times 7 ml). After drying under vacuum at 40° C., 2.66 g of expected product 4 is obtained in the form of beige solid.

Yield 73.5%

II). Second Stage: Dehydration (Obtaining a Compound of Formula (IVa)

1-[N2-[4'-(octyloxy)-[1,1'-biphenyl]-4-yl]carbonyl]-
4-oxo-L-ornithine]-4-[4-(4-hydroxyphenyl)-L-threo-
nine]-5-L-serine-echinocandin B Route 1: Via the Compound of Formula (III'a)

Stage 1: Alkylation

1-[(4R,5R)-4-hydroxy,5-moxy-N2-[[4'-(octyloxy)[1,
1'-biphenyl]-4-yl]carbonyl]-L-ornithine]-4-[4-(4-
hydroxyphenyl)-L-threonine]-5-L-serine echinocan-
din B (III'a)

283 g of product IIIa obtained in the first stage is dissolved in 5.67 liters of methanol. 22.7 g of pyridinium p-toluene sulphonate is added in one go whilst agitating and agitation is carried out for 6 hours under reflux (42° C.) and for 12 hours at ambient temperature. Concentration is carried out under vacuum to two residual volumes then 1.2 liters of water is added. The suspension is agitated for 18 hours. The solid is filtered and rinsed twice with water. After drying in an oven under vacuum at ambient temperature, 270.5 g of expected product is obtained in the form of a beige powder.

Yield 94.2% NMR: (DMSO) Threonine: 8.11 (1H), 4.84 (1H), 4.41 (1H), 1.11 (3H); γHydroxyproline: 4.40 (1H), 1.91–2.27 (2H), 4.42 (1H), 3.67–3.87 (2H); βHydroxy homo tyrosine 7.32 (1H), 4.22 (1H), 4.18 (1H), 2.51–2.44 (2H), 6.96 (2H), 6.65 (2H), 9.03 (1H); Serine: 7.36 (1H), 4.87 (1H), 3.58–3.63 (2H), βHydroxy γmethyl proline: 4.32 (1H), 4.05 (1H), 2.37 (1H), 1.00 (3H), 3.27–3.94 (2H), <<ornithine >>: 7.88 (1H), 4.94 (1H), 4.06 (1H), 8.50 (1H), 4.43 (1H), 3.16 (3H); 1.93–2.03 (2H); Aromatic and octyloxy chain: 7.97 (2H), 7.70 (2H), 7.65 (2H), 7.02 (2H), 4.00 (2H), 1.73 (2H), 1.43 (2H), 1.32 (2H), 1.27–1.28 (6H), 0.87 (3H).

Stage 2: Dehydration 265.3 g of methoxylated product (III'a) obtained above is dissolved in 5.3 liters of dioxane. 71.8 ml of α-acetoxy-isobutyryl bromide (AIBB) is added over 20 minutes. The medium is agitated for 7 hours. 4.1 liters of a saturated aqueous solution of sodium bicarbonate (NaHCO$_3$) is added over 15 minutes. Agitation is carried out for 15 minutes and the dioxane is distilled under vacuum at a temperature which does not exceed 30° C. 3.2 liters of water is added and agitation is carried out for 15 hours at ambient temperature. The solid is filtered and rinsed twice with water. After drying in an oven under vacuum, 251.2 g of expected product is obtained in the form of an ochre solid.

Yield 97.5%

The product is crystallized according to the preparation described below.

Route 2: Starting from Product (IIIa) Obtained in Stage a by the Action of AIBB/MgI$_2$/Dioxane 23.26 g of anhydrous magnesium iodide is suspended in 500 ml of dioxane and agitation is carried out for 30 minutes. 12.25 ml of α-acetoxyisobutyryl bromide (AIBB) is introduced and the ochre suspension is agitated at ambient temperature for 45 minutes. A solution of 50 g of product (IIIa) obtained in the first stage, dissolved in 400 ml of dioxane is added over 1 hour and the addition funnel is rinsed with 25 ml of dioxane. The suspension is agitated for 19 hours at ambient temperature. A solution of 5 g of sodium bicarbonate dissolved in 50 ml of water is introduced over 30 minutes (pH 5–6 at the end of the addition). Agitation is carried out for 2 hours, followed by distilling under vacuum to a residual volume of 250 ml at an internal temperature of less than 35° C. Atmospheric pressure of nitrogen is reestablished, and 200 ml of dimethylformamide is added, followed by distilling under vacuum to a residual volume of 250 ml and this solution is poured at ambient temperature into 2.8 liters of water. After rinsing with DMF, agitation is carried out for 1 hour. The solid is filtered and rinsed with water. The solid is dried for 24 hours under vacuum at 30° C. 46 g of expected product is obtained in the form of beige solid.

Yield: 98.6%

The product is then crystallized according to the method described below.

Route 3: Starting from Product IIIa Obtained in the First Stage by the Action of HBr—AcOH/MgI$_2$/MEK 10 g of product obtained in Stage a) is dissolved in 180 ml of methylethyl ketone (MEK). 4.65 g of anhydrous magnesium iodide and 10 ml of MEK are introduced. Agitation is carried out for 35 minutes at ambient temperature, followed by cooling down to 20° C. 3 ml of a 33% solution of HBr in AcOH is introduced. The suspension is agitated for 4 hours at 20° C. 10 ml of a saturated aqueous solution of NaHCO$_3$ (sodium bicarbonate) is added. Agitation is carried out for 1 hour at 20° C. (dissolution). The solution is poured into 700 ml of water whilst distilling the MEK under vacuum at 40° C. Distillation is carried out to residual volume of 430 ml. 100 ml of water is added and distillation is continued to a residual volume of 430 ml. The operation is repeated twice. The suspension is taken to ambient temperature and agitated overnight. The solid is filtered and washed with 3 times 50 ml of water. After drying under vacuum at ambient temperature, 9.3 g of expected product is obtained in the form of a beige powder. The product is purified by crystallization according to the method described below Yield 94.5% solvents not considered Crystallization of the Product of Formula (IVa) Obtained Above (Route 1, 2 or 3)

10 g of 1-[(N2-[4'-(octyloxy)-[1,1'-biphenyl]-4-yl]carbonyl]-4-oxo-L-ornithine]-4-[4-(4-hydroxyphenyl)-L-threonine]-5-L-serine-echinocandin B (obtained above, route 1, 2 or 3) is dissolved over 1 hour, under agitation and at ambient temperature in 30 ml of dimethylformamide (DMF). 51 mg of initiator (crystals of the product obtained according to routes 1, 2 or 3) is introduced and agitation is carried out for 2 hours. Then 67 ml of acetonitrile is introduced regularly over 2 hours. At the end of the introduction, agitation is carried out for 19 hours, followed by filtering and rinsing with 3 times 10 ml of acetonitrile. After drying under vacuum at ambient temperature, 7.10 g of expected product is obtained in the form of white crystals.

Yield: 71% TLC: rf=0.28 Silica gel 60F$_{254}$, UV 254 nm Mobile phase: CH$_2$Cl$_2$/MeOH/water 86/13/1 NMR: (DMSO) Threonine: 7.94 (1H), 4.50 (1H), 4.25 (1H), 1.18 (3H); γHydroxyproline: 4.39 (1H), 1.93–2.20 (2H), 4.40 (1H), 3.85–3.71 (2H); βHydroxy homo tyrosine 7.53 (1H), 4.06 (1H), 4.25 (1H), 2.44–2.53 (2H), 6.96 (2H), 6.66 (2H), 9.06 (1H); Serine: 7.74 (1H), 4.96 (1H), 3.72 (2H), βHydroxy γmethyl proline: 4.33 (1H), 3.98 (1H), 2.31 (1H), 0.99 (3H), 3.26–4.0 (2H), <<ornithine >>: 8.37 (1H), 3.84–3.64 (2H), 8.11 (1H), 4.83 (1H), 2.82–3.11 (2H); Aromatic and octyloxy chain: 7.91 (2H), 7.69 (2H), 7.66 (2H), 7.02 (2H), 4.02 (2H), 1.74 (2H), 1.43 (2H), 1.32–1.28 (6H), 1.28 (2H), 0.87 (3H).

III: Third Stage: Reducing Amination of the Compound of Formula (IVa) and Obtaining a Compound of Formula (Ia)

1-[4-[(2-aminoyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B Route 1:

8 g of product of formula (IVa) obtained according to Stage II and 2.52 ml of ethylene diamine are dissolved in 80 ml of tetrahydrofuran (THF) whilst agitating for 30 minutes to 1 hour under nitrogen and at ambient temperature. A solution of 0.36 g of titanium tetrachloride dissolved in 80 ml of THF is added over 30 minutes. Agitation is carried out for 1 hour followed by cooling down to 5° C. 3.2 ml of glacial acetic acid dissolved in 16 ml of THF is added. Agitation is carried out for 1 hour at 5° C., followed by cooling down to 0° C. and a solution of 1.04 g of sodium cyanoborohydride dissolved in 24 ml of THF is added over 15 minutes. The reaction medium is left to rise to 5° C. over 30 minutes and agitated for 30 minutes at this temperature. Then left to rise to ambient temperature whilst agitating for 3 hours, followed by distilling under vacuum to 40 ml of the volume, adding a solution of 7.2 g of sodium bicarbonate dissolved in 80 ml of water, distilling under vacuum to a residual volume of 80 ml then 32 ml of methanol and 128 ml of ethyl acetate are added. Agitating is carried out for 10 minutes, followed by decanting, reextracting the aqueous phase with a mixture of ethyl acetate/methanol and distilling all the organic phases under vacuum to a residual volume of 40 ml. 40 ml of DMF is introduced and distilling is continued to a residual volume of 60 ml. This solution is poured into 320 ml of water over 20 minutes and agitated for 15 hours at ambient temperature. If necessary the pH is adjusted to 9–9.5 with dilute soda, followed by filtering and rinsing with an aqueous solution of 1.2 g of sodium bicarbonate (pH 9–9.5). After drying the solid in an oven under vacuum at 30° C. for 18 hours, 8.55 g of expected crude base is obtained in the form of a white solid.

Yield: 100% Isomeric ratio A/B=80/20

Route 2:

10 g of the product of formula (IV) obtained in Stage II) is introduced under agitation and a nitrogen atmosphere into 600 ml of THF. 20 g of 3 Å molecular sieve then 3.16 ml of ethylene diamine and finally 110.4 g of sodium tri-benzyl-L-proline-borohydride are added. The homogeneous solution is agitated at ambient temperature for 6 hours, followed by filtering the molecular sieve and rinsing with THF. The filtrate is distilled to dryness under vacuum at an internal temperature of less than 40° C. 600 ml of a saturated aqueous solution of sodium bicarbonate is added slowly onto the resin obtained whilst agitating. 20 g of Hyflosupercel Kieselgühr filtration agent is added to the suspension and agitation is carried out for 16 hours at ambient temperature, followed by filtering and washing with water. The cake is dissolved by passing through 100 ml of methanol four times. The methanolic filtrate is concentrated to dryness under vacuum without exceeding 40° C. 21.25 g of expected product is obtained.

Route 3

Isolation of the intermediate of the reducing amination reaction (compound of formula IV'a)

1-[4-[N,N'-imidazolidine]-N2-[[4'-(octyloxy)[1,1'-biphenyl]-4-yl]carbonyl]-L-ornithine]-4-[4-(4-hydroxyphenyl)-L-threonine]-5-L-serine echinocandin B A suspension of the product of formula (IVa) obtained in Stage II) in 40 ml of dichloromethane and 0.32 ml of ethylene diamine is agitated for 18 hours. 80 ml of diethyl ether is added and agitation is carried out for 5 hours. The solid is filtered and rinsed several times with diethyl ether. After drying in an oven under vacuum for 15 hours at ambient temperature, 076 g of expected compound is obtained in the form of a white solid. This intermediate is then subjected to the action of a reducing reaction according to preceding routes 1 or 2. This isolated compound is new and forms part of the present invention Yield: 73% MASS:(FAB) MH$^+$ 1100; MNa$^+$: 1122 NMR: Threonine: 8.51 (1H), 4.72 (1H), 4.38 (1H), 1.20 (3H); γHydroxyproline: 4.37 (1H), 1.90–2.22 (2H), 4.42 (1H), 3.88–3.66 (2H); βHydroxy homo tyrosine 7.46 (1H), 4.17 (1H), 4.17 (1H), 2.46 (2H), 6.96 (2H), 6.65 (2H), Serine: 7.47 (1H), 4.84 (1H), 3,65–3.60 (2H), βHydroxy γmethyl proline: 4.22 (1H), 3.93 (1H), 2.29 (1H), 0.95 (3H), 3.22–3.90 (2H), <<ornithine>>: 7.45 (1H), 2.72–3.51 (2H), 9.55 (1H), 4.28 (1H), 1.63–2.12 (2H); Imidazolidine: 2.63–2.94 (2H); 2.78–3.02 (2H); Aromatic and octyloxy chain: 7.87–7.72 (2H, 2H), 7.66 (2H), 7.03 (2H), 4.02 (2H), 1.72 (2H), 1.27 1.32 1.43 (4×2H), 1.29 (2H), 0.88 (3H).

IV)°: Fourth stage: Purification by chromatography of the compound of formula (Ia) obtained previously (according to route 1, 2 or 3) and separation of the two isomers A and B (A or B corresponding to stereoisomers R or S in position 4) Di-trifluoroacetate of 1-[4-[(2-aminoyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B A Prochrom LC 200 column is conditioned with 2.5 g of merck 11763 silica using a methylene chloride (43)-acetonitrile (50)-methanol (7)-water (5)-trifluoroacetic acid (1) mixture as mobile phase. 24 g of the compound obtained above (Stage III, route 1) is dissolved in 126 ml of a mixture composed of acetonitrile (50)-methanol (7)-water (5)-TFA (1). The solution is filtered and 86 ml of methylene chloride is added. This solution is injected into the column. Elution is carried out a flow rate of 76 l/h and a pressure of 14 bars. Detection is carried out at 280 nm, followed by distilling the collected fractions under vacuum at an external temperature of less than 40° C. 36.75 g of product is obtained in the form of the solid di-salt of TFA. Isomeric ratio A/B=99.3/0.7

V): Fifth stage: Purification by chromatography of the di-trifluoroacetate (elimination of the other salts)

A Prochrom LC 50 column is conditioned with 300 g of reversed-phase Daisogel SP 120 no 5/1502 silica, using a water (90)-acetonitrile (10)-trifluoroacetic acid (0.1) mixture as mobile phase. 36.75 g of the salt obtained above in the first chromatography is dissolved in a mixture comprising 57.3 ml of water (90)-acetonitrile (10)-trifluoroacetic acid (0.1) and 26.8 ml of pure acetonitrile. The solution is filtered and this solution is injected into the column. Elution is carried out with water (90)-acetonitrile (10)-trifluoroacetic acid (0.1) in the first instance to remove the mineral salts, then with water (50)-acetonitrile (50)-trifluoroacetic acid (0.1) to remove the product. The fractions collected are distilled under vacuum at an external temperature of less than 40° C. The resultant limpid aqueous solution is lyophilized. 15.59 g of expected product is obtained in the form of a cotonny white solid di-salt of TFA.

Isomeric ratio A/B=99.4/0.6 Cumulative yield of the two chromatographies: 53.8% Yield of the amino reduction: 28.7%

VI): Sixth Stage: Return to the Base

1-[4-[(2-aminoyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B 14.37 g of the compound obtained above, in the form the lyophilized di-trifluoroacetate salt, is dissolved in 143.7 ml of water. Agitation is carried out for 15 minutes under nitrogen and 57.5 ml of a saturated aqueous solution of sodium bicarbonate is added over 15 minutes at ambient temperature. Agitation is carried out for 17 hours. 430 ml of an ethyl acetate/methanol mixture 8/2 is added and agitation is carried out for 15 minutes. The upper organic phase is decanted and the aqueous phase is reextracted with 288 ml of an ethyl acetate (8)-methanol (2) mixture. The organic phases are combined, decanted carefully, and distilled to dryness under vacuum without exceeding 35° C. 143.7 ml of water is added to the dry extract and the suspension is agitated for 30 minutes, followed by filtering and washing with water until there are no more fluorides. After drying the solid under vacuum at 40° C., 10.91 g of expected product is obtained in the form of a white powder.

Yield: 91.6% MICROANALYSIS: (water: 8.8%)

| %  | theory | found        |
|----|--------|--------------|
| C  | 61.020 | 55.3–55.1    |
| H  | 07.224 | 7.5–7.4      |
| N  | 11.437 | 10.3–10.3    |
| F  | 0      | Not detected |

VII): Seventh Stage: Salification (Hydrochloric Acid)

Dihydrochloride of 1-[4-[(2-aminoyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B 10.53 g of compound obtained in the preceding stage is dissolved in 263 ml of methanol whilst agitating for 30 minutes at ambient temperature, followed by filtering and rinsing with twice 31.6 ml of methanol. 2.1 ml of 36% hydrochloric acid is added agitation and under nitrogen at ambient temperature. Agitation is carried out for 30 minutes, followed by distilling to dryness under vacuum without exceeding 35° C. The dry extract is taken up in 105.3 ml of diisopropyl oxide. The suspension obtained is agitated for 2 hours, followed by filtering and washing with twice 21.1 ml of diisopropyl oxide. After drying the solid in an oven under vacuum at 40° C., 10.52 g of expected product is obtained in the form of a white powder.

Yield: 93.7% MICROANALYSIS: (water 5.75%)

| % | theory | found |
|---|--------|-------|
| C | 57.2 | 54.3 |
| H | 6.95 | 7.4 |
| N | 10.73 | 9.8 |
| Cl | 6.03 | 5.95 |
| F | 0 | Not detected |

VIII: Eighth Stage: Crystallization of the Hydrochloric Acid Salt

Dihydrochloride of 1-[4-[(2-aminoyl)amino]-N2-[[4'-(octyloxy)[1,1'-biphenyl]-4-yl]carbonyl]-L-ornithine]-4-[4-(4-hydroxyphenyl)-L-threonine]-5-L-serine echinocandin B 2.75 g of the compound obtained according to Stage VII is dissolved in a mixture of 235.4 ml of acetonitrile and 14.8 ml of demineralized water, while heating under reflux (77.4° C.). Agitation is carried out for 15 minutes at 77° C. then the reaction medium is cooled down to +50° C. over 45 minutes. Initiation is carried out with 41.25 mg of crystallized compound, followed by cooling down regularly to 20° C. over 30 minutes and agitating for 2 hours 15 minutes, to allow crystallization to develop. The suspension is concentrated under vacuum to a residual volume of 55 ml whilst allowing the temperature to rise from 5° C. to 20° C. Normal pressure of nitrogen is re-established, followed by cooling down to 0° C. over 20 minutes, agitating at 0° C. for 17 hours, filtering under nitrogen pressure and rinsing with 11 ml of acetonitrile. After drying the crystallized solid in an oven under vacuum and at 40° C. for 24 hours, 2.29 g of expected product is obtained in the form of a white crystalline solid.

Yield 83.3% HPLC: Rt=5.8 (isomer A); Rt=7.1 (isomer B) Kromasil C18, 15 cm, 4.6 mm, 5 µm Mobile phase: acetonitrile-water-TFA 50/50/0.1 210 nm, 35° C., 1 ml/mn. NMR: CDCl$_3$ 9.07 (m) 1H; 8.48 (d, j=8) 1H; 8.00 (d, j=8) 2H; 7.96 (d, j=8.5) 2H; 7.71 (d, j=8.5) 2H; 7.64 (d, j=8.5) 2H; 7.60 (d, j=9) 1H; 7.37 (d, j=9.5) 1H; 7.02 (d, j=8.5) 2H; 6.97 (d, j=8.5) 2H; 6.65 (d, j=8.5) 2H; 4.90 (m) 1H; 4.77 (m) 1H; 4.66 (m) 1H; 4.45 (m) 1H; 4.42 (m) 1H; 4.39 (m) 1H; 4.34 (s) 1H; 4.26 (m) 1H; 4.22 (m) 1H; 4.08 (m) 1H; 4.01 (t, j=6.5) 2H; 3.88 (m) 3H; 3.70 (m) 21H; 3.51 (m) 2H; 3.48 (m) 1H; 3.31 (m) 2H; 3.28 (m) 1H; 3.16 (m) 2H; 2.53 (dd, j=6 and 13.5) 1H; 2.44 (dd, j=7.5 and 13.5) 1H; 2.27 (m) 1H; 2.25 (m) 1H; 2.15 (m) 2H; 1.94 (m) 1H; 1.74 (m) 2H; 1.44 (m) 2H; 1.22 to 1.40 (m) 8H; 1.13 (d, j=6) 3H; 0.99 (d, j=6.5) 3H; 0.88 (t, j=7) 3H.

EXAMPLE 2

Pharmaceutical Composition Tablets were Prepared Containing

| product of Example 1 | 150 mg |
|---|---|
| Excipient s.q.f | 1 g |

Detail of excipient: starch, talc, magnesium stearate

What is claimed is:

1. A process for the preparation of compounds of formula (I), unsalified forms thereof, and salts thereof

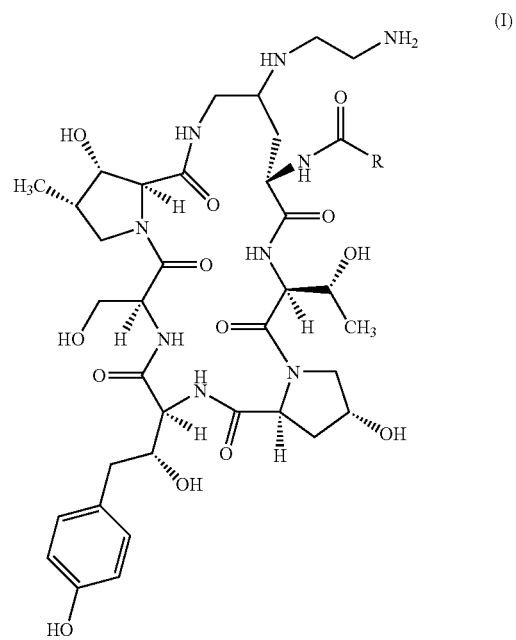

(I)

in which R represents a linear or branched or cyclic chain containing up to 30 carbon atoms, optionally containing one or more heteroatoms and one or more heterocycles, the process comprising:

a) a compound of formula III is provided

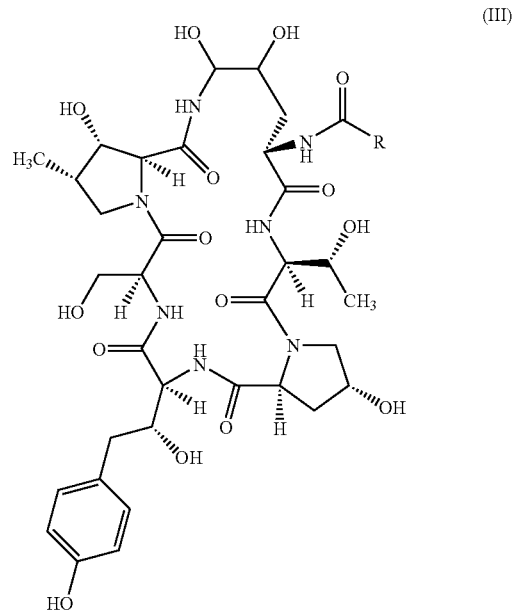

(III)

b) the compound of formula (III) is subjected to an alkylation reaction of the alcohol in position 5 by the action of an alcohol of formula Alk-OH in the presence of pyridinium p-toluenesulfonate (PPTS), Alk representing an alkyl radical containing 1 to 4 carbon atoms, in order to obtain the compound of formula (III')

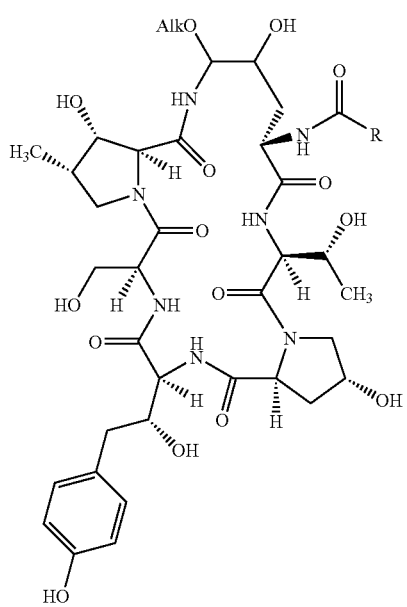

(III')

c) the compound of formula (III) or (III') is subjected to a dehydration reaction, in order to obtain a compound of formula

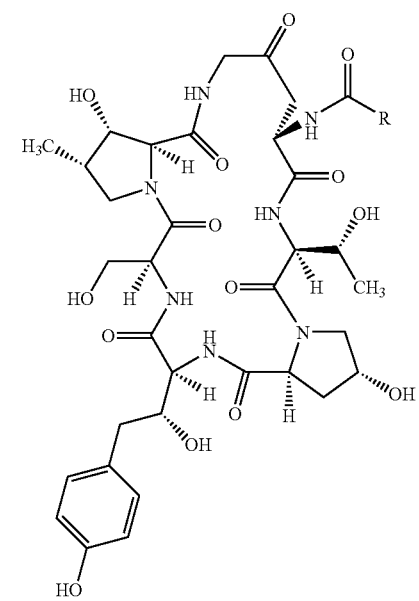

(IV)

d) the compound of formula (IV) is subjected to a reducing amination reaction by the action of ethylene diamine in the presence of a reducing agent comprising $NaBH_3CN$ in the presence of a Lewis acid, or $NaBH(OCOR')_3$, OCOR' representing Boc-L-Pro, Bzl-L-Pro or any other optically active amino acid as well as any other chiral or non chiral carboxylic acid, in order to obtain the compound of formula (I) as defined above, comprising a majority of one of the active isomers, said compound of formula (I) then being optionally subjected to the one or more of the following operations, chromatography, crystallization, the action of a base to form an unsalified compound, and salification.

2. The process according to claim 1 in which the compounds of formulae (I), (III), (III') or (IV) contain an R radical selected from the following groups:

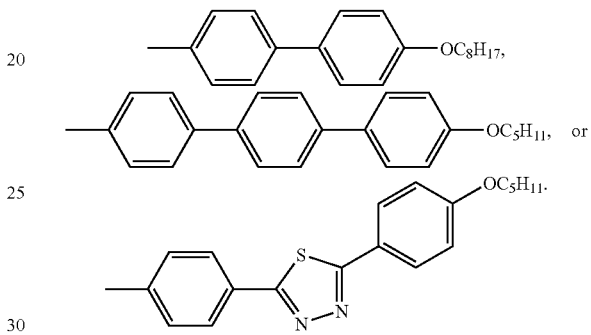

3. The process according to claim 1 in which the compounds of formulae (I), (III), (III'), (IV) contain an R radical selected from the following group:

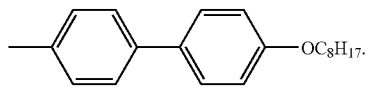

4. The process, according to claim 1 for the preparation of the compound of formula (Ia), unsalified forms thereof, and salts thereof

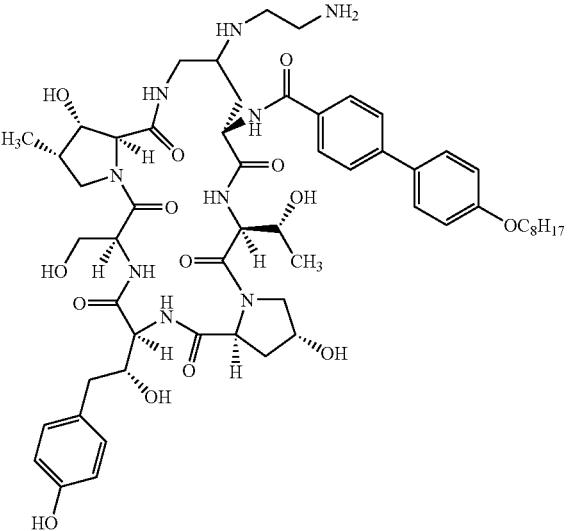

(Ia)

the process comprising:

a) a compound of formula IIIa is provided

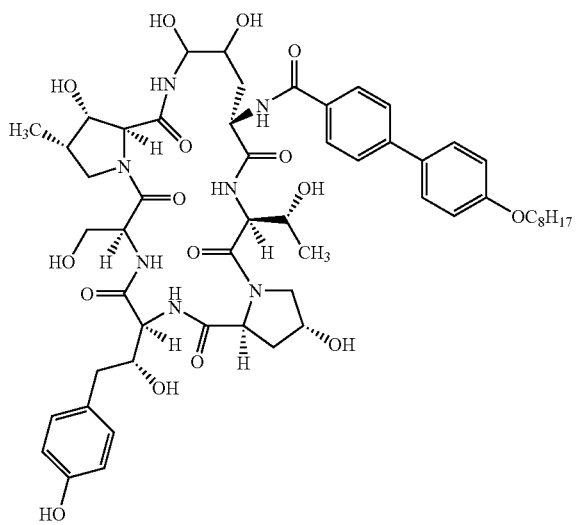
(IIIa)

b) the compound of formula (IIIa) is subjected to an alkylation reaction of the alcohol in position 5 by the action of methanol in the presence of pyridinium p-toluenesulfonate (PPTS), in order to obtain the compound of formula (IIIa')

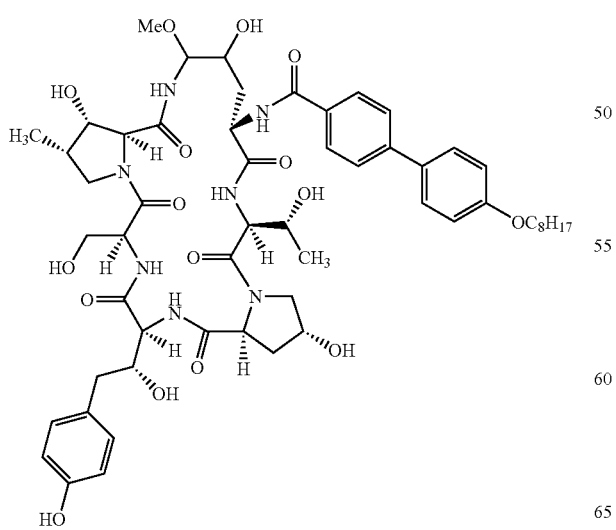
(IIIa')

c) the compound of formula (IIIa) or (IIIa') is subjected to a dehydration reaction, in order to obtain the compound of formula (IVa),

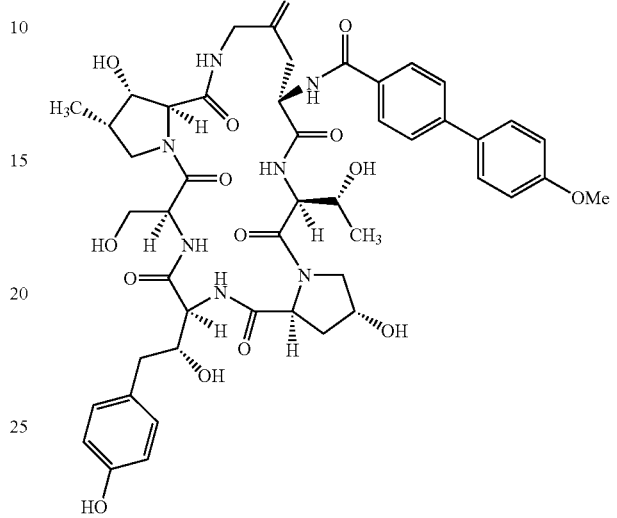
(IVa)

d) the compound of formula (IVa) is subjected to a reducing amination reaction by the action of ethylene diamine in the presence of a reducing agent comprising NaBH$_3$CN coupled with TiCl$_4$, NaBH(Boc-L-Pro)$_3$ or NaBH(Bzl-L-Pro)$_3$, in order to obtain the compound of formula (Ia) as defined above, comprising a majority of the active isomer, said compound of formula (Ia) being optionally subjected to one or more of the following operations, chromatography, crystallization, the action of a base, and salification by the action of hydrochloric acid.

5. The process according to claim 4 characterized in that the compound of formula (Ia) is successively subjected to the following operations:

a) purification by chromatography on silica then by reversed-phase chromatography using a mixture of organic solvents, water and trifluoroacetic acid in order to obtain the trifluoroacetic acid salt of the compound of formula (Ia)

b) the action of a base by the action of an aqueous solution of sodium bicarbonate, in order to obtain the unsalified compound of formula (Ia), and c) salification by the action of hydrochloric acid in order to obtain the corresponding salt, the dihydrochloride of the compound of formula (Ia).

6. The process of claim 4 wherein subpart (a) includes a compound of formula (II)

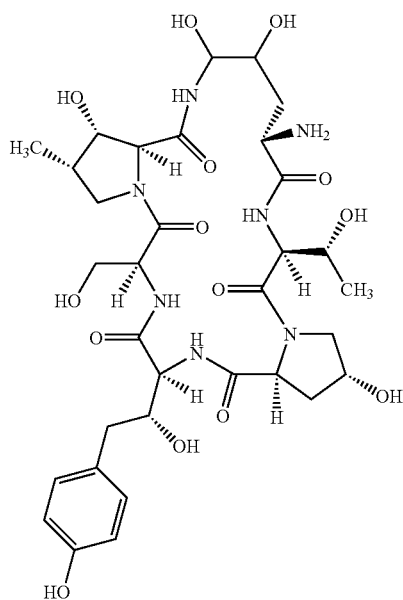

is subjected to the action of an acid of formula $C_8H_{17}$—O-Ph-Ph-$CO_2H$, or an activated form thereof, in order to obtain the compound of formula (IIIa).

7. The process of claim 1 wherein subpart (a) includes a compound of formula (II)

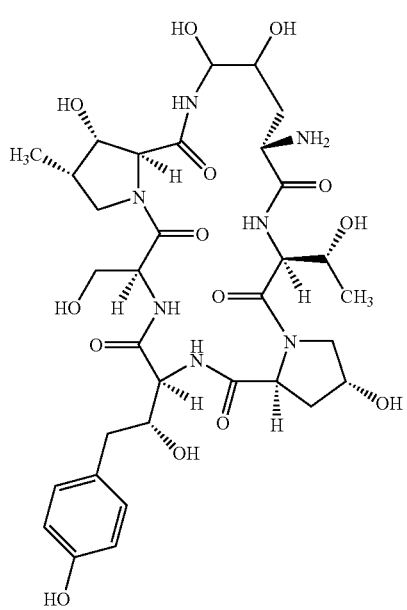

is subjected to the action of an acid of formula R—$CO_2H$, or an activated form thereof, in order to obtain the compound of formula (III).

8. The process according to claim 7, wherein the activation reaction of the acid is carried out in the presence of pentafluorophenol, N-hydroxysuccinimide or optionally N-hydroxybenzotriazole.

9. The process according to claim 7 wherein the acylation reaction in the presence of the acid, or the activated form thereof is carried out in the presence of diisopropylethylamine.

10. The process according to claim 7, wherein the activation reaction then the acylation reaction in the presence of the activated acid, is carried out in the presence of N-methyl pyrrolidone and 4-(4,6-dimethoxy-1,3,5-triazin-2-yl)-4-myl-morpholinium chloride (DMTMM).

11. The process according to claim 1, wherein the dehydration reaction is carried out in the presence of αacetoxy-isobutyryl bromide (AIBB) and optionally $MgI_2$.

12. The process according to claim 1, wherein the dehydration reaction is carried out in the presence of HBr-AcOH and of $MgI_2$.

13. Process according to claim 1, wherein the reducing amination reaction is carried out in the presence of a reducing agent chosen from $NaBH_3CN$ coupled with $TiCl_4$, $NaBH(Boc-L-pro)_3$ and $NaBH(Bzl-L-Pro)_3$.

14. The process according to claim 11 wherein the product originating from the dehydration is purified by crystallization from a DMF/acetone or DMF/AcOEt mixture.

15. The process according to claim 12 wherein the product originating from the dehydration is purified by crystallization from a DNF/acetone or DMF/AcOEt mixture.

16. A process f or the preparation of compounds of formula (I), unsalified forms thereof, and salts thereof

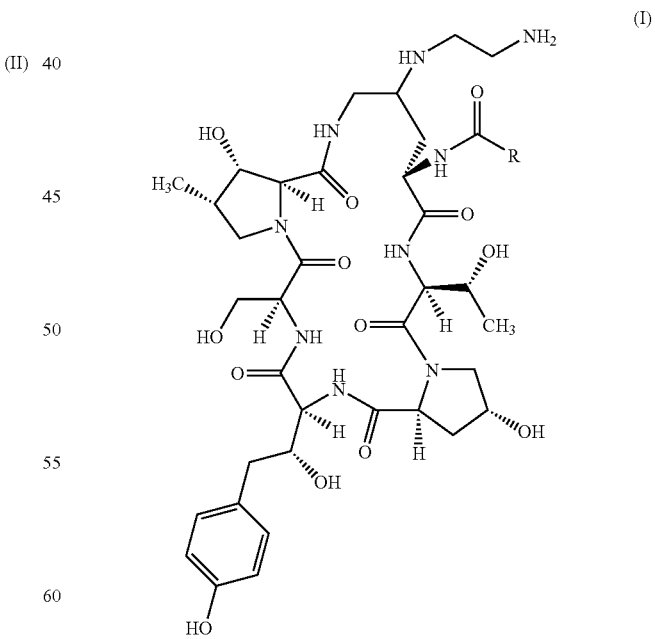

in which R represents a linear or branched or cyclic chain containing up to 30 carbon atoms, optionally containing one or more heteroatoms and one or more heterocycles, the process comprising:

a) a compound of formula (II)

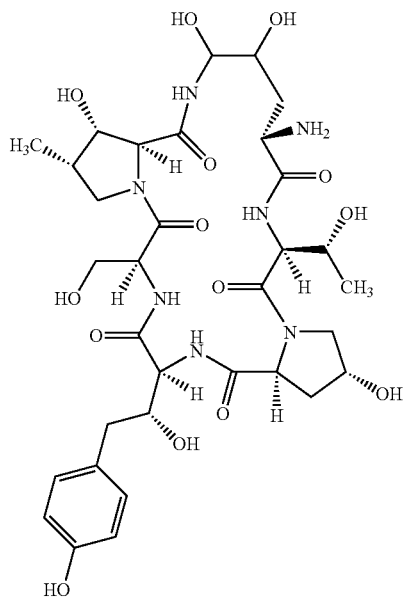

is subjected to the action of an acid of formula R—CO$_2$H, said acid being, in an activated isolated form or non isolated activated form, in order to obtain the compound of formula (III)

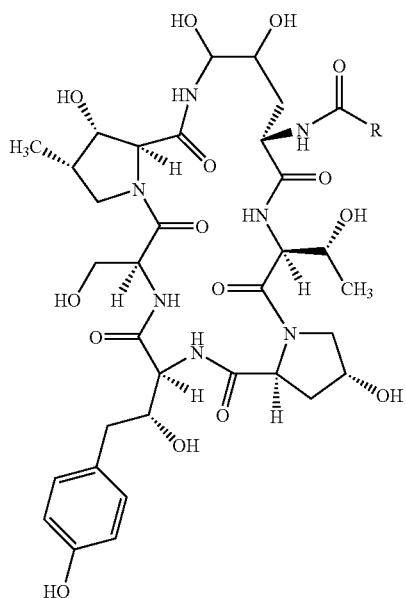

b) optionally, the compound of formula (III) is subjected to an alkylation reaction of the alcohol in position 5 by the action of an alcohol of formula Alk-OH in the presence of pyridinium p-toluenesulfonate (PPTS), Alk representing an alkyl radical containing 1 to 4 carbon atoms, in order to obtain the compound of formula (III')

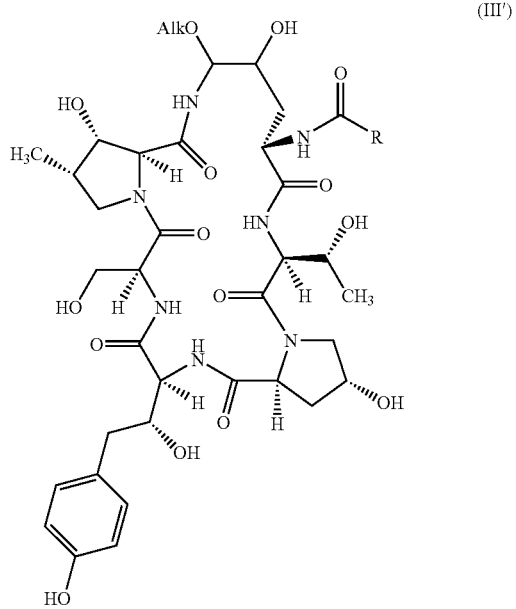

c) the compound of formula (III) or (III') is subjected to a dehydration reaction, in order to obtain a compound of formula (IV)

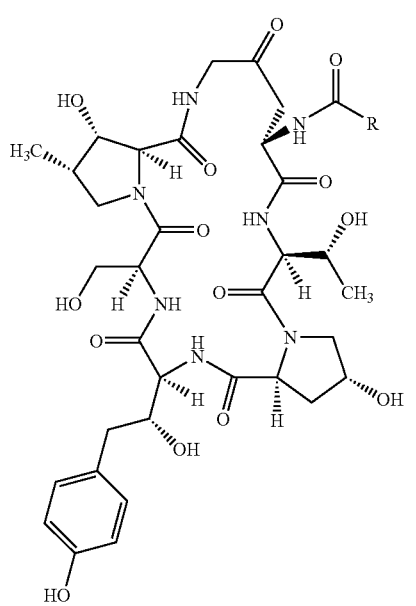

d) the compound of formula (IV) is subjected to a reducing amination reaction by the action of ethylene diamine in the presence of a reducing agent, in order to obtain the compound of formula (I) as defined above, comprising a majority of one of the active isomers, said compound of formula (I) then optionally being subjected to the one or more of the following operations, chromatography, crystallization, the action of a base to form an unsalified compound, and salification; and wherein the activation reaction then the acylation reaction in the presence of the acid, is carried out in the presence of N-methyl pyrrolidone and 4-(4,6-dimethoxy-1,3,5-triazin-2-yl)-4-myl-morpholinium chloride (DMTMM).

17. A process for the preparation of compounds of formula (I), unsalified forms thereof, and salts thereof

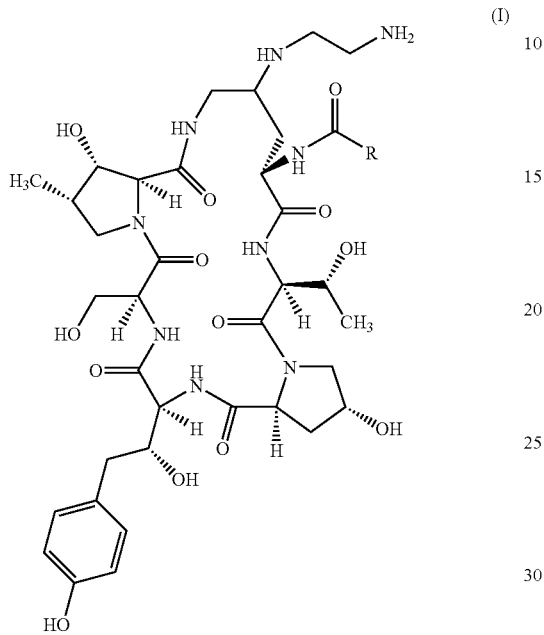

in which R represents a linear or branched or cyclic chain containing up to 30 carbon atoms, optionally containing one or more heteroatoms and one or more heterocycles, the process comprising:

a) a compound of formula (II)

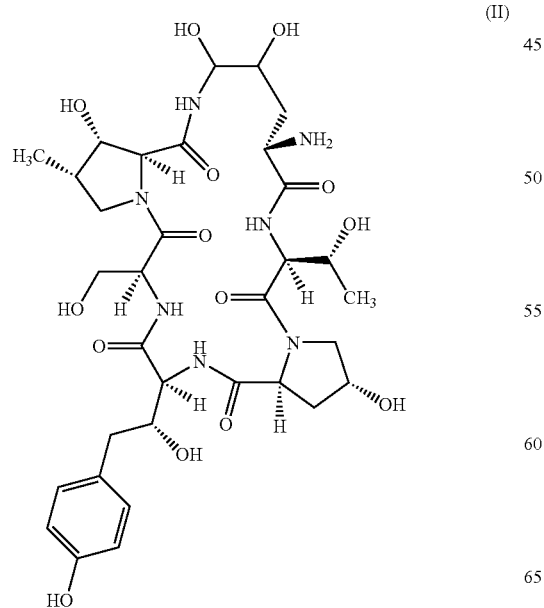

is subjected to the action of an acid of formula R—CO$_2$H, said acid being, in an activated isolated form or non isolated activated form, in order to obtain the compound of formula (III)

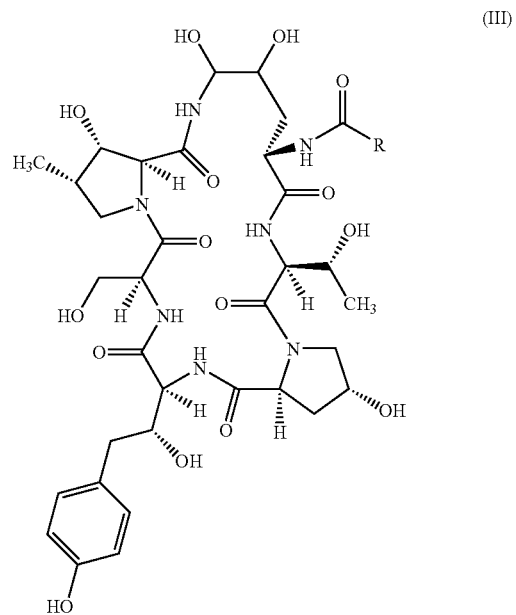

b) optionally, the compound of formula (III) is subjected to an alkylation reaction of the alcohol in position 5 by the action of an alcohol of formula Alk-OH in the presence of pyridinium p-toluenesulfonate (PPTS), Alk representing an alkyl radical containing 1 to 4 carbon atoms, in order to obtain the compound of formula (III')

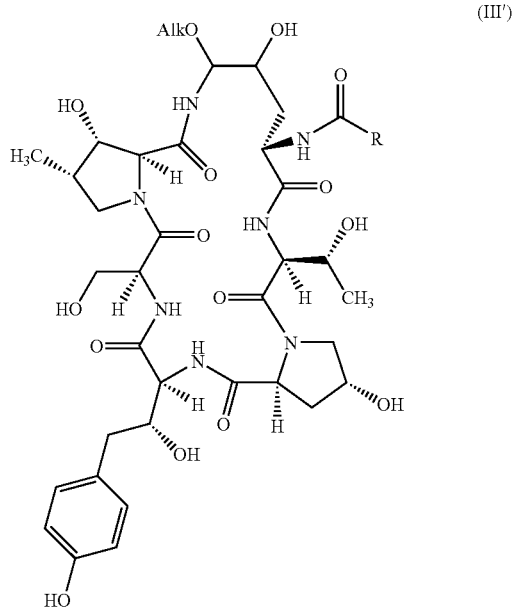

c) the compound of formula (III) or (III') is subjected to a dehydration reaction, in order to obtain a compound of formula (IV)

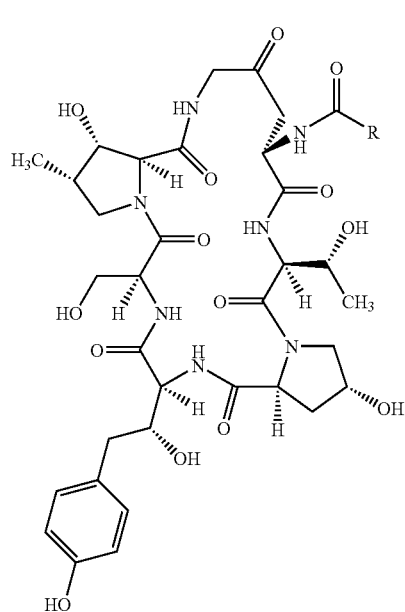

(IV)

d) the compound of formula (IV) is subjected to a reducing amination reaction by the action of ethylene diamine in the presence of a reducing agent, in order to obtain the compound of formula (I) as defined above, comprising a majority of one of the active isomers, said compound of formula (I) then optionally being subjected to the one or more of the following operations, chromatography, crystallization, the action of a base to form an unsalified compound, and salification; and wherein the dehydration reaction is carried out in the presence of α-acetoxyisobutyryl bromide (AIBB) and optionally, MgI₂.

18. The process according to claim 17 wherein the product originating from the dehydration is purified by crystallization from a DMF/acetone or DMF/AcOEt mixture.

19. A process for the preparation of compounds of formula (I), unsalified forms thereof, and salts thereof

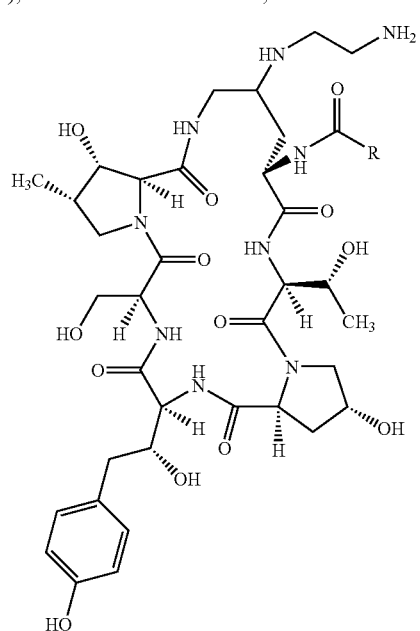

(I)

in which R represents a linear or branched or cyclic chain containing up to 30 carbon atoms, optionally containing one or more heteroatoms and one or more heterocycles, the process comprising:

a) a compound of formula (II)

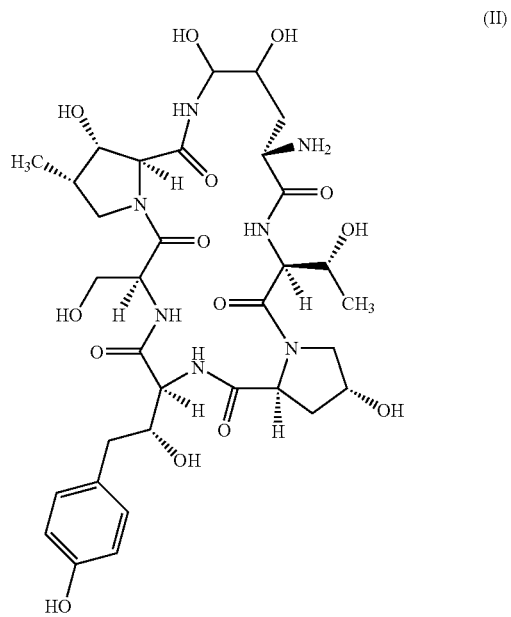

(II)

is subjected to the actien of an acid of formula R—CO₂H, said acid being, in an activated isolated form or non isolated activated form, in order to obtain the compound of formula (III)

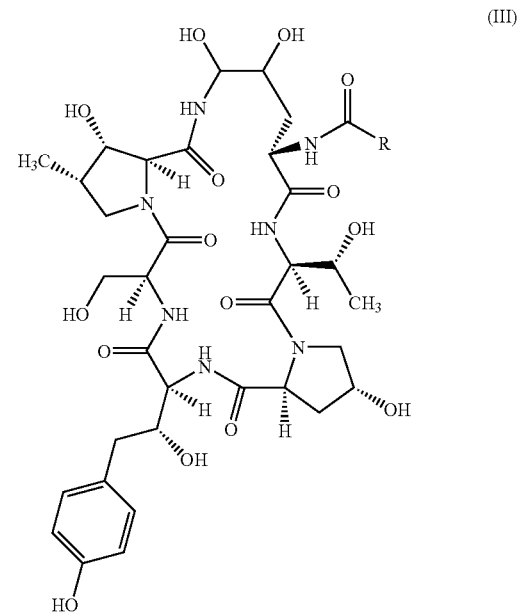

(III)

b) optionally, the compound of formula (III) is subjected to an alkylation reaction of the alcohol in position 5 by the action of an alcohol of formula Alk-OH in the presence of pyridinium p-toluenesulfonate (PPTS), Alk representing an alkyl radical containing 1 to 4 carbon atoms, in order to obtain the compound of formula (III')

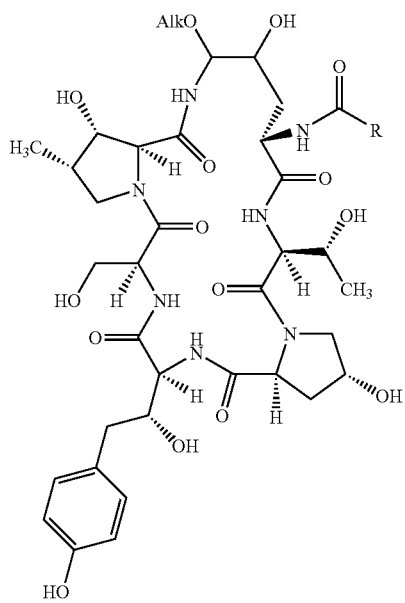

(III')

c) the compound of formula (III) or (III') is subjected to a dehydration reaction, in order to obtain a compound of formula (IV)

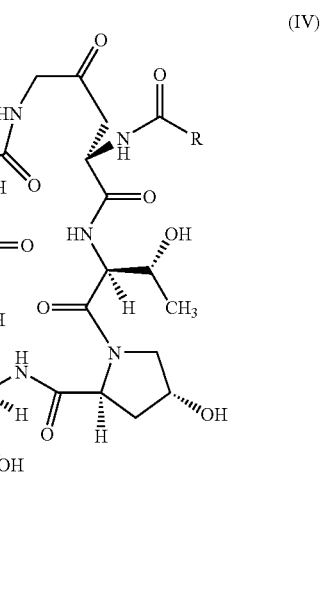

(IV)

d) the compound of formula (IV) is subjected to a reducing amination reaction by the action of ethylene diamine in the presence of a reducing agent, in order to obtain the compound of formula (I) as defined above, comprising a majority of one of the active isomers, said compound of formula (I) then optionally being subjected to the one or more of the following operations, chromatography, crystallization, the action of a base to form an unsalified compound, and salification; and wherein the dehydration reaction is carried out in the presence of HBr-AcOH and of $MgI_2$.

20. The process according to claim 19 wherein the product originating from the dehydration is purified by crystallization from a DMF/acetone or DMF/AcCEt mixture.

* * * * *